US008674151B2

(12) United States Patent
Debuisschert et al.

(10) Patent No.: US 8,674,151 B2
(45) Date of Patent: *Mar. 18, 2014

(54) TWO-STEP HYDROTREATMENT OF A FEED DERIVED FROM A RENEWABLE SOURCE USING A FIRST, METALLIC, CATALYST AND A SECOND, SULPHURIZED, CATALYST

(75) Inventors: Quentin Debuisschert, Rueil Malmaison (FR); Jean Cosyns, Maule (FR); Thierry Chapus, Lyons (FR); Damien Hudebine, Lyons (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 835 days.

This patent is subject to a terminal disclaimer.

(21) Appl. No.: 12/664,136

(22) PCT Filed: Jun. 3, 2008

(86) PCT No.: PCT/FR2008/000754
§ 371 (c)(1),
(2), (4) Date: Aug. 3, 2010

(87) PCT Pub. No.: WO2009/004180
PCT Pub. Date: Jan. 8, 2009

(65) Prior Publication Data
US 2010/0292518 A1 Nov. 18, 2010

(30) Foreign Application Priority Data

Jun. 12, 2007 (FR) ..................................... 07 04226

(51) Int. Cl.
*C07C 1/00* (2006.01)
*C10G 3/00* (2006.01)
*C10G 51/02* (2006.01)
*C10G 45/08* (2006.01)

(52) U.S. Cl.
CPC *C10G 3/42* (2013.01); *C10G 45/08* (2013.01); *C10G 51/02* (2013.01)
USPC .............................. 585/240; 585/242; 44/605

(58) Field of Classification Search
CPC .............. C10G 3/42; C10G 3/46; C10G 3/50; C10G 45/04; C10G 45/08; C10G 51/02; C10G 2300/1011; C10G 2300/1048
USPC .............................. 585/240, 242; 44/605, 606
See application file for complete search history.

(56) References Cited

U.S. PATENT DOCUMENTS

| 7,232,935 | B2* | 6/2007 | Jakkula et al. ................. 585/240 |
| 7,459,597 | B2* | 12/2008 | Koivusalmi et al. .......... 585/733 |
| 7,880,043 | B2* | 2/2011 | Chapus et al. ................. 585/240 |
| 7,888,542 | B2* | 2/2011 | Koivusalmi et al. .......... 585/327 |
| 7,999,142 | B2* | 8/2011 | Kalnes et al. ................. 585/240 |
| 8,026,401 | B2* | 9/2011 | Abhari et al. ................. 585/240 |
| 2004/0230085 | A1 | 11/2004 | Jakkula et al. |
| 2008/0173570 | A1 | 7/2008 | Marchand et al. |

FOREIGN PATENT DOCUMENTS

| EP | 1 693 432 A | 8/2006 |
| FR | 2 910 484 A | 6/2008 |

OTHER PUBLICATIONS

"International Search Report," International Application No: PCT/FR2008/000754, Date of Completion Jan. 8, 2009, Date of completion Jan. 16, 2009, 3pages.
Gusmao J et al: "Utilizatio of Vegetable Oils As an Alternative Source for Diesel-Type Fuel: Hydrocracking on Reduced Ni/SiO2 and Sulphide Ni-Mo/gamma-A1203," Catalysis Today, vol. 5, No. 4, 1989, pp. 533-544, XP003014030, ISSN:0920-5861.
Rocha Filho G N D; Bentes M H S; Brodzki D; Djega-Mariadassou G: "Catalytic Conversion of Hevea-Brasiliensis and Virola-Sevifera Oils to Hydrocarbon Fuels," Journal of the American Oil Chemists, Society vol. 69, No. 3, mars 1992, pp. 266-271 XP002467154.

* cited by examiner

*Primary Examiner* — Nina Bhat
(74) *Attorney, Agent, or Firm* — Millen, White, Zelano & Branigan, P.C.

(57) ABSTRACT

The invention describes a two-step process for hydrotreatment of a feed derived from a renewable source, comprising:
a) a first step, termed a mild pre-hydrogenation step, operating in the presence of a first, metallic, catalyst comprising an active hydrodehydrogenating phase constituted by at least one metal from group VIII and/or at least one metal from group VIB and an amorphous mineral support; and
b) a second step, termed the second treatment step, operating in the presence of a second, sulphurized, catalyst comprising an active hydrodehydrogenating phase constituted by at least one non-noble metal from group VIII and/or at least one metal from group VIB and an amorphous mineral support.

15 Claims, No Drawings

TWO-STEP HYDROTREATMENT OF A FEED DERIVED FROM A RENEWABLE SOURCE USING A FIRST, METALLIC, CATALYST AND A SECOND, SULPHURIZED, CATALYST

This application claims the benefit under National stage entry of PCT/FR2008/000754 filed on Jun. 3, 2008 as well as FR 07/04.226 filed Jun. 12, 2007 under 35 U.S.C. 119.

FIELD OF THE INVENTION

Scarcity and the increase in cost of oil products are driving the search for substitutes. In this context, products from biomass occupy a choice position. Currently, the use of biomass is orientated mainly along two paths: the bioester path which transforms vegetable oils into methyl esters before incorporation into the gas oil pool, and the ethanol path, which transforms sugars and starch into ethanol or ETBE (ethyl tertio-butyl ether) before incorporation into the gasoline pool. Currently, the production costs of such bioproducts are still high compared with fossil fuels and they are only of economic interest if significant fiscal initiatives are provided.

Further, according to the experts, the availability of cultivatable land will not allow more than 10% of the current consumption of fuels to be produced.

In contrast, the production of high purity normal paraffins which can be used in various industries such as the food industry or the petrochemicals industry involves much lower tonnages than those required for fuels. Furthermore, the production of such products may prove to be more profitable than that orientated towards fuels.

Thus, the invention described herein comes into the context of producing high purity normal paraffins, with a number of carbon atoms in the range 6 to 25, preferably in the range 10 to 24 and preferably intended for the production of gas oil or kerosene.

In one aspect, the invention provides a process for the two-step hydrotreatment of a feed derived from a renewable source, comprising:
  a) a first step, termed a mild pre-hydrogenation step, operating in the presence of a first, metallic, catalyst comprising an active hydrodehydrogenating phase constituted by at least one metal from group VIII and/or at least one metal from group VIB and an amorphous mineral support, operating at a temperature in the range 50° C. to 300° C., at a partial pressure of hydrogen in the range 0.1 to 10 MPa, and at an hourly space velocity over the catalyst in the range $0.1\ h^{-1}$ to $10\ h^{-1}$; and
  b) a second step, termed the second treatment step, operating in the presence of a second, sulphurized, catalyst comprising an active hydrodehydrogenating phase constituted by at least one non-noble metal from group VIII and/or at least one metal from group VIB and an amorphous mineral support, operating at a temperature in the range 200° C. to 450° C., at a pressure in the range 1 MPa to 10 MPa, at an hourly space velocity over the catalyst in the range $0.1\ h^{-1}$ to $10\ h^{-1}$ and wherein the total quantity of hydrogen mixed with the feed is such that the hydrogen-to-feed ratio is in the range 50 to 1000 $Nm^3$ of hydrogen per $m^3$ of feed.

One advantage of the invention is that it can provide a concatenation constituted by a first, metallic, catalyst which is selectively more active in hydrogenation, which allows an operation at lower temperatures during this step, followed by a second, sulphurized, catalyst which can maximize the hydrogenation yield.

DESCRIPTION OF THE INVENTION

A two-step process for the hydrotreatment of a feed derived from a renewable source has now been discovered, comprising:
  a) a first step, termed a mild pre-hydrogenation step, operating in the presence of a first, metallic, catalyst comprising an active hydrodehydrogenating phase constituted by at least one metal from group VIII and/or at least one metal from group VIB and an amorphous mineral support, operating at a temperature in the range 50° C. to 300° C., at a partial pressure of hydrogen in the range 0.1 to 10 MPa, and at an hourly space velocity over the catalyst in the range $0.1\ h^{-1}$ to $10\ h^{-1}$; and
  b) a second step, termed the second treatment step, operating in the presence of a second, sulphurized, catalyst comprising an active hydrodehydrogenating phase constituted by at least one non-noble metal from group VIII and/or at least one metal from group VIB and an amorphous mineral support, operating at a temperature in the range 200° C. to 450° C., at a pressure in the range 1 MPa to 10 MPa, at an hourly space velocity over the catalyst in the range $0.1\ h^{-1}$ to $10\ h^{-1}$ and wherein the total quantity of hydrogen mixed with the feed is such that the hydrogen-to-feed ratio is in the range 50 to 1000 $Nm^3$ of hydrogen per $m^3$ of feed.

In accordance with step a) of the process of the invention, the first, metallic, catalyst comprises an active hydrodehydrogenating phase constituted by at least one metal from group VIII and/or at least one metal from group VIB, the metal from group VIII preferably being selected from nickel and cobalt, palladium and platinum; more preferably, the metal from group VIII is nickel, and the metal from group VIB is preferably selected from molybdenum and tungsten; more preferably, the metal from group VIB is molybdenum.

Advantageously, combinations of the following metals are used: nickel-molybdenum and cobalt-molybdenum.

In accordance with a highly preferred implementation of step a) of the process of the invention, said first, metallic, catalyst employed in the first step, said mild pre-hydrogenation step, comprises an amorphous mineral support and an active hydrodehydrogenating phase constituted by at least one metal from group VIII, the metal from group VIII being nickel.

The quantity of metal from group VIII, noble or non-noble, is advantageously in the range 0.5% to 20% by weight, preferably in the range 5% to 10% by weight with respect to the total mass of catalyst. The quantity of metal from group VIB is advantageously in the range 0.5% to 20% by weight, preferably in the range 7% to 17% by weight with respect to the total mass of catalyst.

In accordance with a preferred implementation of step a) of the process of the invention, said first, metallic, catalyst used in the first step, said mild pre-hydrogenation step, comprises an amorphous mineral support selected from alumina, silica and silica-alumina.

In accordance with the process of the invention, a first step, termed the mild pre-hydrogenation step, is carried out in the presence of a first, metallic, catalyst comprising an active hydrodehydrogenating phase constituted by at least one metal from group VIII and/or at least one metal from group VIB and an amorphous mineral support and is followed by a second step, termed the second treatment step, which is carried out in the presence of a second, sulphurized, catalyst comprising an active hydrodehydrogenating phase constituted by at least one non-noble metal from group VIII and/or at least one metal from group VIB and an amorphous mineral support.

In accordance with a preferred implementation of step b) of the process of the invention, said second, sulphurized, catalyst comprises an active hydrodehydrogenating phase constituted by at least one non-noble metal from group VIII and/or at least one metal from group VIB, the non-noble metal from group VIII preferably being selected from nickel and cobalt; preferably, the non-noble metal from group VIII is nickel, and the metal from group VIB is preferably selected from molybdenum and tungsten; preferably, the metal from group VIB is molybdenum.

In accordance with a highly preferred implementation of step b) of the process of the invention, said second, sulphurized, catalyst used in the second step, termed the second treatment step, comprises an amorphous mineral support and an active hydrodehydrogenating phase constituted by at least one non-noble metal from group VIII, the non-noble metal from group VIII being nickel, and at least one metal from group VIB, the metal from group VIB being molybdenum.

The total quantity of oxides of metals from groups VIB and VIII in said second, sulphurized, catalyst is advantageously in the range 5% to 40% by weight, and preferably in the range 7% to 30% by weight with respect to the total mass of catalyst.

The weight ratio expressed as the metallic oxide between the metal (or metals) from group VIB to the metal (or metals) from group VIII in said second, sulphurized, catalyst is advantageously in the range 20 to 1, and preferably in the range 10 to 2.

A preferred second, sulphurized, catalyst employed in step b) of the process of the invention advantageously comprises a nickel oxide (NiO) content in the range 0.5% to 10% by weight, preferably in the range 1% to 5% by weight, and a molybdenum oxide ($MoO_3$) content in the range 1% to 30% by weight, preferably in the range 5% to 25% by weight on an amorphous mineral support, the percentages being expressed as a % by weight with respect to the total mass of catalyst.

In accordance with a preferred implementation of step b) of the process of the invention, said second, sulphurized, catalyst comprises at least one doping element selected from phosphorus, silicon, fluorine and boron, the quantity of doping element by weight of the oxide of said element being less than 20% with respect to the total mass of catalyst, preferably less than 10% with respect to the total mass of catalyst.

This doping element may advantageously be introduced into the matrix or, preferably, be deposited on the support. It is also possible to deposit silicon on the support, alone or with phosphorus and/or boron and/or fluorine.

In accordance with a preferred implementation of step b) of the process of the invention, said second, sulphurized, catalyst comprises an amorphous mineral support selected from the group formed by alumina, silica, silica-aluminas, magnesia and clays, used alone or as a mixture. Said support may advantageously also comprise other compounds such as, for example, oxides selected from the group formed by boron oxides, zirconia, titanium oxide and phosphoric anhydride, used alone or as a mixture.

Highly preferably, an alumina support is used, and still more preferably an 1, 8 or 7 alumina support.

In accordance with step b) of the process of the invention, said second catalyst is a sulphurized catalyst; thus, it is advisable to maintain it in contact with a partial pressure of $H_2S$ which is sufficient to prevent desulphurization in the presence of hydrogen at the reaction temperatures. To this end, and in a conventional manner, hydrogen sulphide or at least one sulphur-containing compound which decomposes into $H_2S$ under the conditions of the second step is added to the feed or directly to the reactor.

Examples of a sulphur-containing compounds which may be cited are dimethyldisulphide (DMDS), carbon disulphide ($CS_2$), organic polysulphides, mercaptans, sulphides, disulphides, oxygen-containing sulphur compounds, and elemental sulphur, dissolved and/or partially in suspension.

In accordance with a preferred implementation of the process of the invention, the first step, termed the mild pre-hydrogenation step, is operated in the presence of a first, metallic, catalyst comprising an alumina support and an active hydrodehydrogenating phase constituted by at least one metal from group VIII, the metal from group VIII being nickel, and the second step, termed the second treatment step, which is operated in the presence of a second, sulphurized, catalyst comprising an alumina support and an active hydrodehydrogenating phase constituted by at least one non-noble metal from group VIII and at least one metal from group VIB, the non-noble metal from group VIII being nickel and the metal from group VIB being molybdenum.

The feeds derived from renewable sources used in the hydrotreatment process of the invention are advantageously constituted by oils and fats of animal or vegetable origin, or mixtures of such feeds, containing triglycerides and/or fatty acids and/or esters. Possible vegetable oils which may be included are unrefined or completely or partially refined oils derived from the following plants: rapeseed, sunflower, soya, palm, palm-nut, olive, coconut; this list is not limiting. Possible fats which may be cited are any animal fats such as lard or fats composed of residues from the food industry or derived from the restaurant industry.

The feeds defined hereby contain triglyceride structures and/or fatty acids and their esters, with fatty chains containing in the range 6 to 25 carbon atoms.

These feeds are practically or completely free of sulphur-containing and nitrogen-containing compounds and do not contain aromatic hydrocarbons.

Advantageously, prior to the two-step hydrotreatment process of the invention, the feed may undergo a step for pre-treatment or pre-refining in order to eliminate, by means of an appropriate treatment, contaminants such as metals, alkaline compounds, alkaline-earths and phosphorus, for example over ion exchange resins.

Examples of appropriate treatments are heat treatments and/or chemical treatments which are well known to the skilled person.

In accordance with a preferred implementation of the hydrotreatment process of the invention, the first step of said process, said mild pre-hydrogenation step, consists of mild pre-hydrogenation of at least 50% of the double bonds contained in the hydrocarbon chain of the fatty acids of said feed, preferably at least 80% of the double bonds, more preferably at least 90% of the double bonds and still more preferably at least 99% of the double bonds, followed by a second treatment step consisting of hydrogenation of at least 50% of the ester functions contained in the hydrocarbon chain of the fatty acids of said feed, preferably at least 80% of the double bonds, more preferably at least 90% of the ester functions and still more preferably at least 99% of the ester functions.

The double bonds of the hydrocarbon chains may be assayed using several analytical methods:
measuring the iodine value, consisting of measuring the quantity of di-iodine ($I_2$) capable of bonding to the unsaturated bonds of the hydrocarbon chains. The measured value is thus expressed in mg of $I_2$ bound to 100 g of product. Applied to fatty acids, the iodine value is, for example, 90 for oleic acid, 181 for linoleic acid and 274 for linolenic acid. The iodine value is measured for the methyl esters of vegetable oils (MEVO) using the standard method EN 14111. Other standard methods which may be cited are the ASTM D 1959 and ASTM D 5554 methods.

The bromine index or bromine number is measured using potentiometry. The bromine index is applicable for contents of less than 1000 mg/100 g of product, using the standard ASTM D 2710. The bromine number concerns assaying by potentiometry for contents of more than 1 g/100 g of product, using the standard ASTM D 1159.

The presence of ester functions is demonstrated using an infra-red spectrometry method. The principle of the method resides in the presence of an infra-red band specific to the ester function. The hydrogenation of ester functions thus results in disappearance of the specific band detected in the infra-red.

The first step for treatment of said feed consisting of mile pre-hydrogenation is intended to saturate the double bonds contained in the hydrocarbon chain of the fatty acids of the feed, in order to prevent secondary reactions of the double bonds such as, for example, polymerization reactions leading to the formation of coke or gums. This first, pre-hydrogenation, step is advantageously operated in the presence of the first, metallic, catalyst described above at a temperature in the range 50° C. to 300° C., preferably in the range 50° C. to 200° C. and more preferably in the range 100° C. to 200° C., and at a partial pressure of hydrogen in the range 0.1 MPa to 10 MPa. The hourly space velocity over the catalyst is in the range 0.1 $h^{-1}$ to 10 $h^{-1}$.

The quantity of hydrogen consumed during this mild pre-hydrogenation step is in the range 0.5% to 1% by weight of hydrogen with respect to the feed.

The effluent from this first mild pre-hydrogenation step is then brought into contact in a second step for treatment of said feed with the second sulphurized catalyst described above, said second treatment step being operated at a temperature in the range 200° C. to 450° C., preferably in the range 220° C. to 350° C. The pressure is in the range 1 MPa to 10 MPa, preferably in the range 2 MPa to 6 MPa. The hourly space velocity over the catalyst is in the range 0.1 $h^{-1}$ to 10 $h^{-1}$. The feed is brought into contact with the catalyst in the presence of hydrogen. The total quantity of hydrogen mixed with the feed is such that the ratio of hydrogen to feed is in the range 50 to 1000 $Nm^3$ of hydrogen per $m^3$ of feed, preferably in the range 100 to 500 $Nm^3$ of hydrogen per $m^3$ of feed. The hydrogen consumption during this second step is typically in the range 2% to 3% by weight with respect to the initial feed.

Said second step for treatment of the feed, carried out under more severe operating conditions than those of said first step for mild pre-hydrogenation, advantageously accomplishes hydrogenation of at least 50% of the ester functions contained in the hydrocarbon chain of the fatty acids of the feed, preferably at least 80%, more preferably at least 90% and still more preferably at least 99% of the ester functions.

The presence of ester functions is demonstrated using the infra-red spectrometry method described above.

At least a portion, preferably all, of the hydrotreated effluent from the two-step hydrotreatment process of the invention then undergoes one or more separation steps.

The aim of this step is to separate the gas from the liquid, and in particular to recover hydrogen-rich gas which may also contain gases such as carbon monoxide (CO), carbon dioxide ($CO_2$) and propane, and at least one liquid hydrocarbon effluent constituted by at least 50% by weight of straight chain n-paraffins, preferably at least 80% by weight, more preferably at least 90% by weight and still more preferably at least 98% by weight of straight-chain n-paraffins and with a number of carbon atoms in the range 6 to 25.

The measurement of the quantity of paraffins (normal paraffins and iso-paraffins) is carried out using a chromatographic method. It is coupled with a mass spectrometer. This method also provides access to the quantities of olefins, naphthenes and aromatics (PONA analysis).

A portion of the water formed during the two-step process for hydrotreatment of feeds derived from renewable sources of the process of the invention is contained in the liquid hydrocarbon effluent and at least a portion thereof, preferably all, is advantageously separated from the hydrocarbon liquid effluent. Thus, separation may be followed by a step for elimination of the water.

The mixture of hydrogen gas ($H_2$), carbon monoxide (CO), carbon dioxide ($CO_2$) and propane which is separated may then advantageously undergo treatments which are known to the skilled person to eliminate carbon monoxide (CO) and carbon dioxide ($CO_2$) and separate the hydrogen from the propane, this latter advantageously being able to be sent to a steam cracking furnace dedicated to steam cracking liquefied gas.

Example 1

Step a) Two-Step Hydrotreatment of a Feed Derived from Renewable Sources

1) First, Mild Pre-Hydrogenation, Step

A fixed bed of 40 g of mild pre-hydrogenation catalyst based on nickel on alumina containing 15% by weight, calculated as the nickel and pre-reduced, was charged into a first stage constituted by a reactor which had been adjusted to provide isothermal operation. 100 g/h of pre-refined rapeseed oil with the composition given below was sent over this fixed bed.

TABLE 2

| Composition of feed derived from renewable sources | | |
|---|---|---|
| Fatty acid glycerides | Nature of fatty chain | % by weight |
| Palmitic | C16:0 | 4 |
| Palmitoleic | C16:1 | <0.5 |
| Stearic | C18:0 | 2 |
| Oleic | C18:1 | 61 |
| Linoleic | C18:2 | 20 |
| Linoleic | C18:3 | 9 |
| Arachidic | C20:0 | <0.5 |
| Gadoleic | C20:1 | 1 |
| Behenic | C22:0 | <0.5 |
| Erucic | C22:1 | <1 |

100:1 NTP of hydrogen per liter of feed (NTP=normal temperature and pressure) was introduced at 150° C. at a pressure of 4 MPa. After separating out the excess hydrogen, a mixture of glycerides was obtained at a yield of very slightly above 100%. The pre-hydrogenated effluent contained the same chains as the starting feed in which the double bonds had been almost completely hydrogenated. The resulting hydrogen consumption was of the order of 0.9% by weight with respect to the feed.

2) Second Feed Treatment Step

The pre-hydrogenated mixture from this first step was sent directly and in its entirety to a second reactor functioning under isothermal conditions and with a fixed bed charged with 89 g of a catalyst for the second feed treatment step, said catalyst comprising a hydrodehydrogenating phase constituted by nickel and molybdenum and having a nickel oxide content of 4.3% by weight and a molybdenum oxide content of 21.5% by weight on an alumina support, the catalyst having been sulphurized. 150:1 NTP of $H_2$ per liter of feed was introduced into this reactor maintained at 300° C. at a pressure of 4 MPa.

Step b): Separation of Effluent from Step a)

The whole of the hydrotreated effluent from step a) of the process of the invention was separated in order to recover a hydrogen-rich gas and a paraffinic liquid hydrocarbon effluent which was separated from the water produced. The yields obtained are indicated in the table below:

TABLE 3

| Compounds | Yields (wt %/feed) |
| --- | --- |
| CO | 0.42 |
| $CO_2$ | 3.53 |
| $C_1$ | 0.10 |
| $C_2$ | 0.12 |
| $C_3$ | 3.21 |
| $C_4$ | 0.03 |
| $C_5$ | 0.05 |
| Paraffinic liquid hydrocarbon effluent | 85.7 |
| $H_2O$ | 8.52 |
| Total | 101.68 |
| $H_2$ consumed (wt %/feed) | 1.68 |

The paraffinic hydrocarbon liquid effluent obtained thereby was analyzed using gas chromatography coupled with a mass spectrometer: it was constituted by 98% by weight of n-paraffins with a number of carbon atoms of 6 to 25 and 2% of $C_{17}$ to $C_{21}$ iso-paraffins. More than 95% of the n-paraffins were $C_{16}$ to $C_{22}$.

The invention claimed is:

1. A process comprising subjecting a feed derived from a renewable source, to a two-step hydrotreatment comprising:
   a) a first mild pre-hydrogenation step, operating in the presence of a first, metallic, catalyst comprising an active hydrodehydrogenating phase constituted by at least one metal from group VIII and/or at least one metal from group VIB and an amorphous mineral support, operating at a temperature in the range of 50° C. to 300° C., at a partial pressure of hydrogen in the range 0.1 to 10 MPa, and at an hourly space velocity over the catalyst in the range 0.1 $h^{-1}$ to 10 $h^{-1}$; and
   b) a second treatment step, operating in the presence of a second, sulphurized, catalyst comprising an active hydrodehydrogenating phase constituted by at least one non-noble metal from group VIII and/or at least one metal from group VIB and an amorphous mineral support, operating at a temperature in the range of 200° C. to 450° C., at a pressure in the range 1 of MPa to 10 MPa, at an hourly space velocity over the catalyst in the range of 0.1 $h^{-1}$ to 10 $h^{-1}$ and wherein the total quantity of hydrogen mixed with the feed is such that the hydrogen-to-feed ratio is in the range 50 to 1000 $Nm^3$ of hydrogen per $m^3$ of feed.

2. A process according to claim 1, in which said first, metallic, catalyst comprises an active hydrodehydrogenating phase constituted by at least one metal from group VIII and/or at least one metal from group VIB, the at least one metal from group VIII being selected from nickel and cobalt, palladium and platinum, and the at least one metal from group VIB being selected from molybdenum and tungsten.

3. A process according to claim 2, in which said first, metallic, catalyst comprises an active hydrodehydrogenating phase constituted by at least one metal from group VIII and/or at least one metal from group VIB, the at least one metal from group VIII being nickel and the at least one metal from group VIB being molybdenum.

4. A process according to claim 1, in which said first, metallic, catalyst comprises an amorphous mineral support and an active hydrodehydrogenating phase constituted by at least one metal from group VIII, the at least one metal from group VIII being nickel.

5. A process according to claim 1 wherein the first metallic catalyst comprises, in which a quantity of metal from group VIII in the range of 0.5% to 20% by weight with respect to the total mass of catalyst and the quantity of metal from group VIB the range of 0.5% to 20% by weight with respect to the total mass of catalyst.

6. A process according to claim 1, in which said first, metallic, catalyst comprises an amorphous mineral support selected from alumina, silica and silica-alumina.

7. A process according to claim 1, in which said second, sulphurized, catalyst comprises an active hydrodehydrogenating phase constituted by at least one non-noble metal from group VIII and/or at least one metal from group VIB, the at least one non-noble metal from group VIII being selected from nickel and cobalt and the at least one metal from group VIB being selected from molybdenum and tungsten.

8. A process according to claim 7, in which the non-noble metal from group VIII is nickel and the metal from group VIB is molybdenum.

9. A process according to claim 1, in which said second, sulphurized, catalyst comprises an amorphous mineral support and an active hydrodehydrogenating phase constituted by at least one non-noble metal from group VIII, the non-noble metal from group VIII being nickel, and at least one metal from group VIB, the metal from group VIB being molybdenum.

10. A process according to claim 1 comprising a total quantity of oxides of metals from groups VIB and VIII in said second, sulphurized, catalyst in the range of 5% to 40% by weight with respect to the total mass of the second catalyst.

11. A process according to claim 1, in which said second, sulphurized, catalyst comprises a quantity of nickel oxide (NiO) in the range of 0.5% to 10% by weight with respect to the total mass of the second catalyst, and a quantity of molybdenum oxide ($MoO_3$) in the range 1% to 30% by weight with respect to the total mass of catalyst, on an amorphous mineral support.

12. A process according to claim 7, in which said second, sulphurized, catalyst comprises an amorphous mineral support selected from alumina, silica, silica-aluminas, magnesia and clays, taken alone or as a mixture.

13. A process according to claim 12, in which said support is an alumina support.

14. A process according to claim 1, in which the first step is operated in the presence of a first, metallic, catalyst comprising an alumina support and an active hydrodehydrogenating phase constituted by at least one metal from group VIII, the at least one metal from group VIII being nickel, and in which the second step is operated in the presence of a second, sulphurized, catalyst comprising an alumina support and an active hydrodehydrogenating phase constituted by at least one non-noble metal from group VIII and at least one metal from group VIB, the at least one non-noble metal from group VIII being nickel and the at least one metal from group VIB being molybdenum.

15. A hydrotreatment process according to claim 1, in which the feeds derived from a renewable source are oils and fats of animal or vegetable origin, or mixtures of such feeds, containing triglycerides and/or fatty acids and/or esters, said vegetable oils being either unrefined or completely or partially refined, said feeds containing triglyceride structures and/or fatty acid structures and esters thereof, with fatty chains containing in the range 6 to 25 carbon atoms.

* * * * *

UNITED STATES PATENT AND TRADEMARK OFFICE
CERTIFICATE OF CORRECTION

PATENT NO.         : 8,674,151 B2                                            Page 1 of 1
APPLICATION NO.    : 12/664136
DATED              : March 18, 2014
INVENTOR(S)        : Debuisschert et al.

It is certified that error appears in the above-identified patent and that said Letters Patent is hereby corrected as shown below:

In the Claims

Column 8, line 14 reads "VIB the range of 0.5% to 20% by weight with respect to the", should read --VIB is in the range of 0.5% to 20% by weight with respect to the--.

Signed and Sealed this
Ninth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,674,151 B2                                       Page 1 of 1
APPLICATION NO.  : 12/664136
DATED            : March 18, 2014
INVENTOR(S)      : Debuisschert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1067 days.

Signed and Sealed this
Twenty-ninth Day of September, 2015

Michelle K. Lee
*Director of the United States Patent and Trademark Office*